United States Patent [19]

Inouye

[11] Patent Number: 5,023,181

[45] Date of Patent: Jun. 11, 1991

[54] PROCESS FOR PREPARING A CALCIUM-DEPENDENT OXYGENASE

[75] Inventor: Satoshi Inouye, Yokohamashi, Japan

[73] Assignee: Chisso Corporation, Osaka, Japan

[21] Appl. No.: 218,299

[22] Filed: Jul. 13, 1988

[30] Foreign Application Priority Data

Aug. 19, 1987 [JP] Japan ................................ 62-206165

[51] Int. Cl.$^5$ .......................... C12N 9/02; C12Q 1/26
[52] U.S. Cl. ...................................... 435/189; 435/25
[58] Field of Search ................................. 435/25, 189

[56] References Cited

PUBLICATIONS

Shimomura et al., *Nature* 256: 236–238, (1975).

Izutsu et al., *Biochem. Biophys. Res. Comm.* 49 (4): 1034–1039, (1972).

*Primary Examiner*—Douglas W. Robinson
*Assistant Examiner*—M. Meller
*Attorney, Agent, or Firm*—Wenderoth, Lind & Ponack

[57] ABSTRACT

A process for preparing a Ca-dependent oxygenase having a continuously photogenic performance for a long time when it is continuously added to a substrate such as coelenterazine, which process comprises treating an apoaequorin obtained from natural photoprotein aequorin or an apoaequorin obtained by subjecting an apoaequorin to recombinant DNA technique, with a reducing agent such as 2-mercaptoethanol and reacting the resulting apoaequorin with a metal ion such as calcium ion, preferably in the presence of a substrate coelenterazine.

2 Claims, 3 Drawing Sheets

- $E_1$: REDUCING AGENT-UNTREATED APOAEQUORIN
- $E_2$: REDUCING AGENT-TREATED APOAEQUORIN
- $S_1$: SUBSTRATE COELENTERAZINE
- $S_2$: OXYGEN ($O_2$)
- $P_1$: COELENTERAMIDE
- $P_2$: CARBON DIOXIDE ($CO_2$)
- $P_3$: LIGHT
- 2MeSH: 2-MERCAPTOETHANOL
- EDTA: ETHYLENEDIAMINE TETRAACETIC ACID
- $Ca^{2+}$: CALCIUM ION
- CDO: CALCIUM-DEPENDENT OXYGENASE

PROCESS FOR PREPARING A CALCIUM-DEPENDENT OXYGENASE

BACKGROUND OF THE INVENTION

1. Field of the Invention

This invention relates to a process for preparing a calcium-dependent oxygenase.

More particularly it relates to a process for preparing an enzyme having a continuously photogenic performance when the enzyme is continuously added to a substrate, by treating the protein part of a Ca-binding photoprotein aequorin with a reducing agent and a metal ion.

2. Description of the Related Art

A Ca-binding photoprotein aequorin existent in nature emits light within several seconds when coelenterazine as an emitter present in the protein is oxidized in the presence of trace Ca ion. Since this series of reactions is irreversible, it is difficult to maintain the light-emission continuously and for a long time.

In order to solve the above-mentioned problem, the present inventor has performed extensive research employing the techniques of gene engineering and protein engineering.

If an apoaequorin(protein part) obtained from natural aequorin and an apoaequorin prepared according to a recombinant DNA technique (see Japanese patent application Nos. Sho 60-280259/1985, Sho 61-249098/1986, Sho 61245108/1986, Sho 61-245109/1986, Sho 62-126373/1987 and Sho 62-126374/1987) can be subjected to enzyme reaction for a long time, as in the case of conventional enzymes, then the general-purpose properties of the apoaequorin in the aspect of detection method are enhanced as compared with the above-mentioned instantaneously photogenic aequorin and it is possible to detect continuous light-emission by means of X-ray film, etc. This makes it possible to utilize the aequorin as a substitute for radioisotope; hence it has a utility.

The gist of the present invention consists in utilizing the catalytic function of the protein part (apoaequorin) of the Ca-binding photoprotein aequorin i.e. a function at which a substrate coelenterazine is decomposed and emits light by the addition of $Ca^{2+}$ in the presence of oxygen.

As to natural aequorin or aequorin prepared through recombinant DNA, apoaequorin-oxygen-coelenterazine is present in a complex form and this instantaneously emits light by means of $Ca^{2+}$ ion. This reaction is irreversible and when a substrate is added and also a reducing agent is added, only a very weak emitted light can be detected; hence it has a poor utility.

The present inventor further has performed extensive research on a treating method with a reducing agent taking into account the change in the higher order structure of apoaequorin, addition of $Ca^{2+}$ ion, etc. and a process of preparing an apoaequorin having a sufficient utility i.e. a Ca-dependent oxygenase which catalyzes a continuous light emission.

As a result, we have found that the above-mentioned problems can be solved by a Ca-dependent oxygenase obtained by treating apoaequorin with a reducing agent in a suitable concentration to obtain a reduction type apoaequorin and reacting this apoaequorin with a metal ion preferably in the presence of a substrate coelenterazine.

SUMMARY OF THE INVENTION

The present invention consists in the following main constitution (1) and constitutions (2) to (4) as embodiments thereof:

(1) A process for preparing a Ca-dependent oxygenase, which comprises treating an apoaequorin ($E_1$) with a reducing agent and treating the resulting apoaequorin ($E_2$) with a metal ion;

(2) a process according to the item (1) wherein said apoaequorin ($E_1$) is an apoprotein obtained from natural photoprotein aequorin or an apoaequorin obtained by subjecting a apoaequorin to recombinant DNA technique;

(3) a process according to the item (1) wherein coelenterazine or its derivatives are used as a substrate for said oxygenase; and (4) a process according to the item (1) wherein calcium ion or strontinum ion is used as said metal ion.

BRIEF DESCRIPTION OF THE DRAWINGS

In FIGS. 1 and 2,

A, A': apoaequorin not subjected to treatment with reducing agent,

B: substrate coelenterazine

C: 2-mercaptoethanol

D: $CaCl_2$

↓ : indicates injection of the respective agents.

Figure 3:
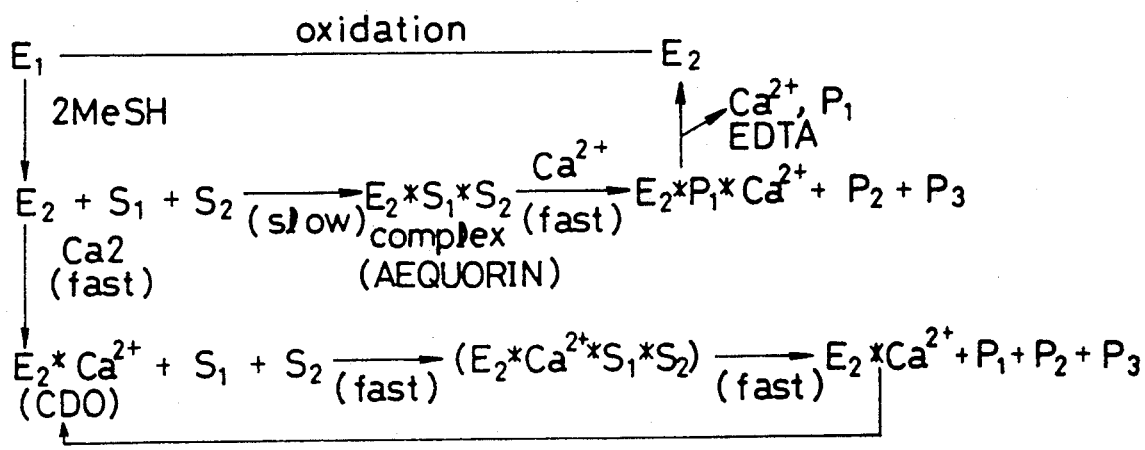

FIG. 3 shows a flowsheet illustrating a reaction relationship between aequorin and Ca-dependent oxygenase.

DETAILED DESCRIPTION OF PREFERRED EMBODIMENTS

The constitutions and effectiveness of the present inventions will be described in more detail.

A. Apoaequorin used in the present invention ($E_1$)

This is an apoprotein obtained by isolating and purifying natural photoprotein (aequorin) in a conventional manner.

As to the isolating and purifying method, for example, a suitable quantity of $Ca^{2+}$ source (e.g. $CaCl_2$) is added to aequorin to allow it to emit light, followed by adding a suitable quantity of $Ca^{2+}$-removing agent such as EDTA (ethylenediaminetetraacetic acid) to the reaction material after light-emission to remove $Ca^{2+}$ linked to aequorin, and subjecting the material obtained by the removal to isolating treatment such as isolation according to column chromatography to obtain apoaequorin.

The apoaequorin used in the present invention may also be an apoaequorin directly produced in *Escherichia coli* using a plasmid which makes the expression of apoaequorin possible according to recombinant DNA technique (see the Example mentioned later, with regard to the prior literature), or an apoaequorin obtained by further purifying the above-mentioned apoaequorin for example according to anion-exchange chromatography.

B. Reduction of apoaequorin:

Reduction of apoaequorin referred to herein means scission of the disulfide bond (—S—S—) of the protein. The reducing agent used for such a reduction has no particular limitation, but its examples are 2-mercaptoethanol, dithiothreitol, etc. The reduction conditions have no particular limitation, but for example, a mixed solution of the apoaequorin and a reducing agent is allowed to stand at 0° to 40° C., preferably 0° C. to 10° C., for 10 minutes to 10 hours, preferably 30 minutes to 3 hours.

C. Preparation and measurement of Ca-dependent oxygenase

Preferably a substrate coelenterazine is mixed with the reduction type apoaequorin obtained in the above item B, followed by setting the resulting mixed solution in a reaction cuvette in a luminophotometer and then pouring e.g. 30 mM $CaCl_2$ solution in a suitable quantity therein. The mixing order of the substrate coelenterazine and the 30 mM $CaCl_2$ solution may be reversed. A continuous light-emissions of the thus set Ca-dependent oxygenase is recorded in terms of relative light units (see Example mentioned later and FIGS. 1 and 2).

In addition, FIG. 3 shows a relationship between aequorin and Ca-dependent oxygenase.

According to the present invention, by treating enzyme part (apoaequorin) isolated from natural aequorin or an apoaequorin prepared according to recombinant DNA technique with a suitable concentration of a reducing agent to obtain a reduction type apoaequorin, followed by adding thereto Ca ion and a substrate coelenterazine, it is possible to allow the resulting material to continuously emit light. Further, since the above continuous light-emission becomes possible, the emitted light is photographed by X-ray film, etc. whereby finally it is possible to detect Ca ion.

EXAMPLE

I. Preparation of apoaequorin (1) Preparation thereof from natural aequorin 30 mM $CaCl_2$ (500 µl) is added to natural aequorin (100 µg) to emit light, followed by adding 100 mM EDTA (ethylenediaminetetraacetic acid) (500 µl) to remove $Ca^{2+}$ and subjecting the resulting material to Sephadex G 25 (trademark) column chromatography (100×10 φ mm), to obtain the objective apoaequorin.

(2) Preparation thereof according to recombinant DNA technique

The apoaequorin was produced using a plasmid which can effect apoaequorin expression in *Escherichia coli*. Preparation of apoaequorin is disclosed in Japanese patent application Nos. Sho 60-280259/1985, Sho 61-249098/1986, Sho 61-245108/1986, Sho 61-245109/1986, Sho 62-126373/1987, Sho 62-126374/1987 and Biochemistry, 1986, 25, 8425-8429, (Inoue et al). Or, apoaequorin is obtained by further purifying the above apoaequorin according to anion exchange chromatography (DEAE-Cellulofine (trademark), DEAE-Sephacel (trademark), etc.).

II Treatment of apoaequorin with a reducing agent (Preparation of reduction type apoaequorin → Ca-dependent oxygenase)

To a solution (2 ml) of apoaequorin (100 µg) is added 2-mercaptoethanol (100 µl) capable of effecting scission of the disulfide bond (—S—S— bond) of protein, followed by allowing the mixture to stand at 4° C. for one hour or longer to prepare a reduction type apoaequorin.

III. Measurement method and measurement of Ca-dependent oxygenase

The reduction type apoaequorin (2 µl) prepared in the above item (2) is mixed with a substrate coelenterazine (2 µl) (100 µg/ml), followed by setting the mixture in a reaction cuvette of a Lumiphotometer-TD4000 type (trademark of an instrument made by Laboscience Company, Tokyo), pouring 30 mM $CaCl_2$ solution (100 µl) therein or pouring 30 mM $CaCl_2$ solution (100 µl) in the reduction type apoaequorin (2 µl), mixing these, pouring a substrate coelenterazine (2 µl) in the mixture and recording a continuously emitted light in terms of relative light units (rlu) by means of a recorder.

Figure 1:
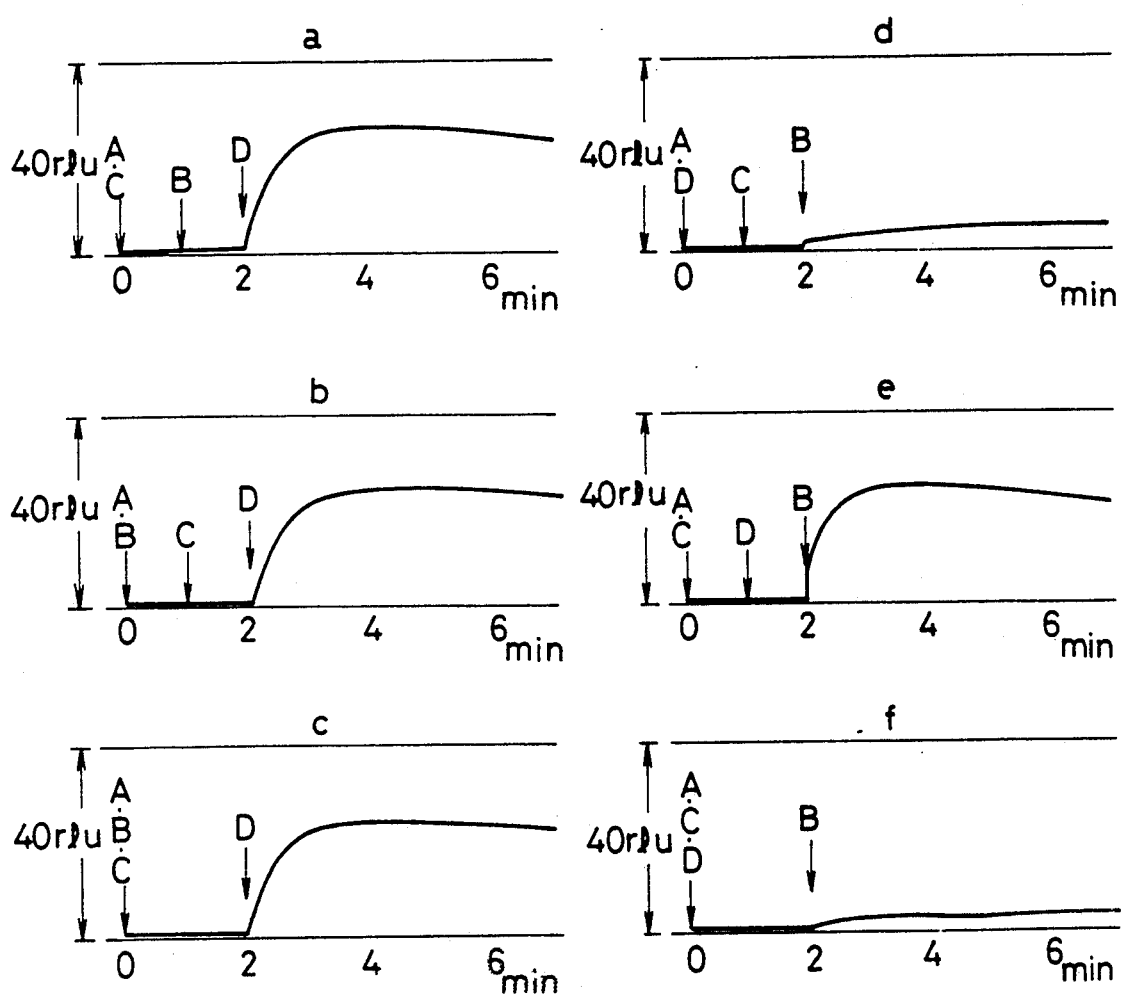
FIGS. 1 to 3 each show an explanatory view of the Example of the present invention.
Figure 2:
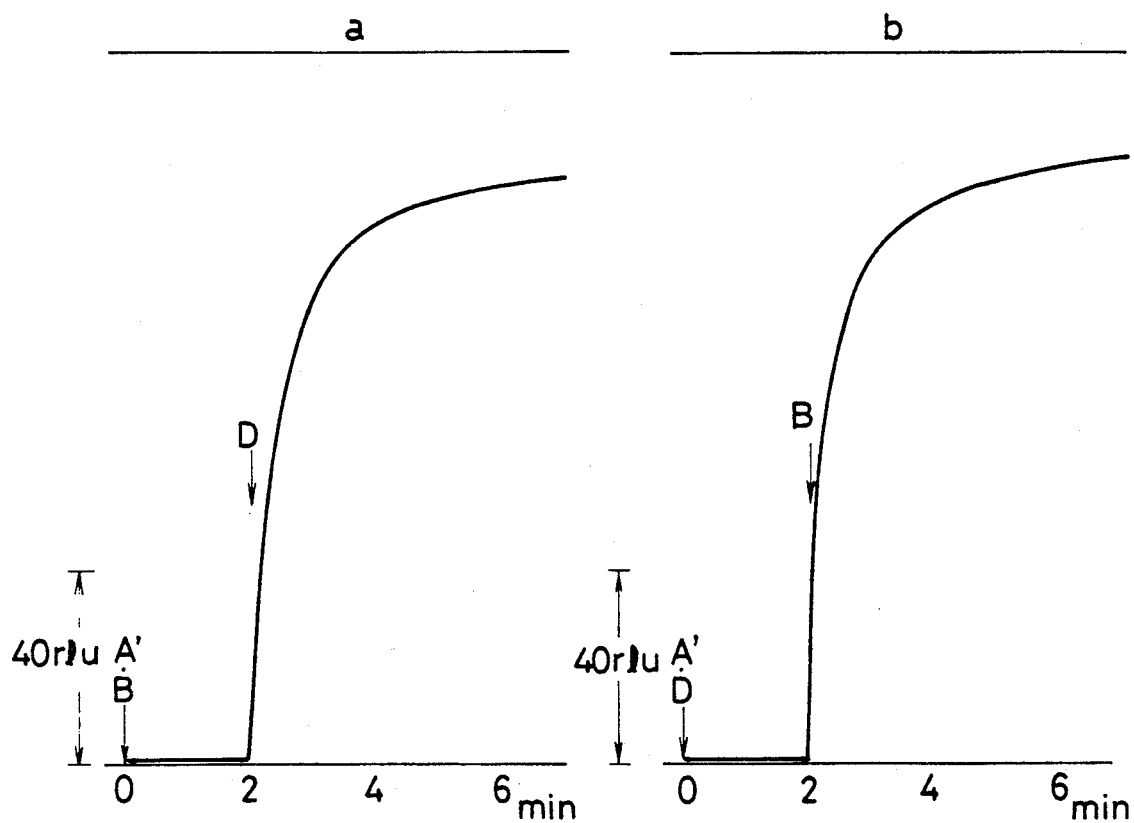

The emitted light curves of the reducing agent-untreated and -treated materials and the effect of the mixing order of the enzyme, the substrate and $Ca_{2+}$ ion are shown in FIGS. 1 and 2.

FIG. 1 is directed to reducing agent-untreated apoaequorin, and the symbols in FIG. 1 have to the following meanings:

A: reducing agent-untreated apoaequorin (2 µl)
B: substrate coelenterazine (2 µl)
C: 2-mercaptoethanol (2 µl)
D: $CaCl_2$ (100 µl)

Arrow mark indicates a pour point.

a to c in FIG. 1 refer to a continuous light-emission due to addition of $CaCl_2$.

d to f in FIG. 1 refer to a continuous light-emission due to addition of coelenterazine.

When Ca ion is first added, only a very weak emitted light is detected as shown in d and f. Further, treatment with 2-mercaptoethanol for about one minute exhibits an effect of about 10 times those in the above cases, as shown in a, b, c and e in FIG. 1.

Thus, the cases of apoaequorin previously treated with a reducing agent (treatment for 12 hours) are shown in FIG. 2.

In FIG. 2, the symbol a shows a continuous emitted light generated when a reducing agent-treated apoaequorin (A') was mixed with a substrate coelenterazine (B) and after 2 minutes, the mixture was poured in Ca (D), and The symbol b shows a continuous emitted light generated when a reducing agent-treated apoaequorin (A') was mixed with Ca solution (D) and after 2 minutes, a substrate coelenterazine was poured. In the case of FIG. 2 (a, b), it is apparent that as compared with the untreated apoaequorin in FIG. 1, the photogenic activity is higher by about 5 times and yet continuous light-emission to the same extent occurs. Namely, a Ca-dependent oxygenase exhibiting a continuous functioning of apoaequorin due to the treatment with a reducing agent has been prepared.

FIG. 3 illustrates such a series of reactions including aequorin and explains a continuous light-emission due to treatment with a reducing agent.

What we claim is:

1. A process for preparing a $Ca^{2+}$-dependent oxygenase, which comprises treating apoaequorin with at least one reducing agent selected from the group consisting of 2-mercaptoethanol and dithiothreitol, followed by reacting $Ca^{2+}$ ion with the resulting apoaequorin and then mixing coelenterazine as a substrate with the reduced apoaequorin.

2. A process for preparing a $Ca^{2+}$-dependent oxygenase, with comprises treating apoaequorin with at lest one reducing agent selected from the group consisting of 2-mercaptoethanol and dithiothreitol, followed by mixing the resulting apoaequorin with coelenterazine as a substrate and then reacting the resulting mixture solution with $Ca^{2+}$ ion.

* * * * *